United States Patent [19]

Beck

[11] 4,012,224

[45] Mar. 15, 1977

[54] HERBICIDAL USE OF β-AMINOATROPONITRILES

[75] Inventor: James Richard Beck, Indianapolis, Ind.

[73] Assignee: Eli Lilly and Company, Indianapolis, Ind.

[22] Filed: Dec. 2, 1975

[21] Appl. No.: 636,884

[52] U.S. Cl. .............................. 71/105; 260/465 E
[51] Int. Cl.² ............................................ A01N 9/20
[58] Field of Search ....................................... 71/105

[56] References Cited

UNITED STATES PATENTS

| | | | |
|---|---|---|---|
| 3,250,798 | 5/1966 | Shulgin | 71/105 X |
| 3,513,186 | 5/1970 | Kuderna | 71/105 X |
| 3,656,932 | 4/1972 | Scheuermann et al. | 71/105 |
| 3,828,091 | 8/1974 | Strong | 260/465 F |
| 3,865,863 | 2/1975 | Field et al. | 71/105 X |

OTHER PUBLICATIONS

Novelli et al., Tetrahedron 24, 2481–2484 (1968).
C.A., 61, Eiden et al., 14559h (1964).
C.A., 47, Strukov, 8690c (1952).

*Primary Examiner*—Joseph Paul Brust
*Attorney, Agent, or Firm*—Joseph A. Jones; Everet F. Smith

[57] ABSTRACT

A class of β-aminoatroponitriles are useful herbicides. The compounds have a meta-substituent, or no substituent, on the phenyl ring, and the amino group may be substituted with lower alkyl groups.

7 Claims, No Drawings

HERBICIDAL USE OF β-AMINOATROPONITRILES

BACKGROUND OF THE INVENTION

This invention belongs to the art of agricultural chemistry, and provides herbicidal methods making use of a class of compounds not previously known to be agriculturally useful. Unwanted plants growing in cropland, as well as in fallow land, consume soil nutrients and water, and compete with crops plants for sunlight. Thus, weeds constitute a drain on the soil and cause measurable losses in the yield of crops. Herbicides are therefore recognized as necessary for obtaining the greatest benefit from the land.

Some of the compounds used in this invention are presently known in the chemical art. For example, Novelli, *Tetrahedron* 24, 2481–84 (1968), showed the synthesis of β-dimethylamino- and diethylaminoatroponitrile.

Some nitriles have been used in agricultural chemistry. Strong, U.S. Pat. No. 3,828,091, taught the herbicidal use of β-alkylthioatroponitriles, for example.

SUMMARY OF THE INVENTION

This invention provides to the agricultural chemical art new herbicidal methods using compounds of the formula

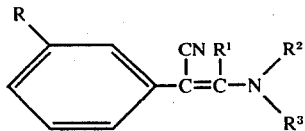

wherein R represents
 hydrogen,
 chloro,
 fluoro,
 bromo or
 trifluoromethyl;
$R^1$, $R^2$ and $R^3$ independently represent hydrogen, methyl or ethyl.

DESCRIPTION OF THE PREFERRED EMBODIMENT

The following exemplary compounds are presented to assure that skilled readers understand the invention. The compounds below do not bound the invention, of course, but are merely typical of it.
 β-amino-β-ethylatroponitrile
 β-dimethylamino-β-ethylatroponitrile
 m-chloro-β-diethylamino-β-methylatroponitrile
 β-ethylmethylamino-m-fluoro-β-methylatroponitrile
 m-bromo-β-dimethylamino-β-methylatroponitrile
 β-ethylamino-β-methyl-m-trifluoromethylatroponitrile
 β-aminoatroponitrile
 m-chloro-β-dimethylamino-β-ethylatroponitrile
 m-chloro-β-methyl-β-methylaminoatroponitrile
 β-diethylamino-m-fluoro-β-methylatroponitrile
 m-bromo-β-dimethylaminoatroponitrile
 β-ethyl-β-methylamino-m-trifluoromethylatroponitrile The preferred compounds of this invention are β-dimethylamino-m-trifluoromethylatroponitrile, β-dimethylamino-m-fluoroatroponitrile, m-chloro-β-dimethylaminoatroponitrile, β-dimethylamino-β-methyl-m-trifluoromethylatroponitrile, and β-diethylamino-m-trifluoromethylatroponitrile.

The compounds used in this invention are readily prepared from appropriately phenyl-substituted phenylacetonitriles. The preferred synthesis proceeds by reaction with a di(methyl or ethyl)acetal of di(methyl or ethyl)formamide, or, when a β-methyl or β-ethyl compound is to be made, with an acetal of acetamide or propionamide, respectively. The reaction readily goes neat or in dimethylformamide at temperatures from about 50° C. to about 120° C. The reaction is discussed in the literature, for example, by Novelli, supra.

Alternatively, the compounds may be prepared by first acylating the phenylacetonitrile with a (methyl or ethyl) alkanoate in the presence of alkoxide ion to form the corresponding β-hydroxyatroponitrile. A formate is used to make compounds without a β-alkyl group, and an acetate or propionate to make products with β-methyl or ethyl groups. The reaction is carried out at approximately 0°–25° C., and alkoxide ion is best supplied as an alkali metal alkoxide.

The hydroxy compound is then alkylated with a (methyl or ethyl) halide or sulfate in the presence of a base. Suitable bases include such compounds as silver oxide, sodium hydroxide and potassium carbonate. The alkylation is performed either neat, where the alkylating agent is a liquid, or in such solvents as alkanols, dimethylformamide and dimethylsulfoxide. Temperatures in the range of 25°–100° C. may be used, depending on the reactants in use.

Finally, the alkoxy group is replaced with an amine bearing the $R^2$ and $R^3$ substituents to form the desired herbicide. The general reaction conditions are the same as the conditions in the previous step.

All of the starting compounds used in the synthesis of the compounds of this invention are commonly known and are readily obtainable by organic chemists.

A few typical syntheses will be shown to assure that chemists can obtain any desired compound of this invention. All of the compounds discussed below were identified by nuclear magnetic resonance analysis, elemental analysis, and, in some cases, by mass spectroscopy.

EXAMPLE 1

β-dimethylaminoatroponitrile

A 5.85 g. portion of phenylacetonitrile was heated on the steam bath with 5.95 g. of dimethylformamide diethyl acetal for 6 hours. The reaction mixture was then cooled with the precipitation of crystalline product. The liquid portion of the mixture was decanted, and the solids were recrystallized twice from benzene-hexane to produce 1.4 g. of β-dimethylaminoatroponitrile, m.p. 76–80° C.

|   | Theoretical | Found |
|---|---|---|
| C | 76.71% | 77.01% |
| H | 7.02 | 7.01 |
| N | 16.27 | 16.05 |

EXAMPLE 2

β-dimethylamino-m-trifluoromethylatroponitrile

The process of Example 1 was repeated using 9.25 g. of m-trifluoromethylphenylacetonitrile and 5.95 g. of the acetal to produce 3.75 g. of β-dimethylamino-m-trifluoromethylatroponitrile, m.p. 110–112° C.

|   | Theoretical | Found |
|---|---|---|
| C | 60.00% | 60.21% |
| H | 4.62 | 4.87 |
| N | 11.66 | 11.85 |

EXAMPLE 3

β-dimethylamino-m-fluoroatroponitrile

The process of Example 1 was followed with 1.4 g. of m-fluorophenylacetonitrile and 1.2 g. of dimethylformamide dimethyl acetal to produce 1.2 g. of β-dimethylamino-m-fluoroatroponitrile, m.p. 114° C.

|   | Theoretical | Found |
|---|---|---|
| C | 68.46% | 68.65% |
| H | 5.83 | 5.84 |
| N | 14.73 | 14.85 |

EXAMPLE 4 m-chloro-β-dimethylaminoatroponitrile

A 6.1 g. portion of m-chlorophenylacetonitrile and 4.8 g. of dimethylformamide dimethyl acetal were used as in Example 1 to produce 1 g. of m-chloro-β-dimethylaminoatroponitrile, m.p. 99°–100° C.

|   | Theoretical | Found |
|---|---|---|
| C | 63.93% | 63.51% |
| H | 5.36 | 5.20 |
| N | 13.55 | 13.75 |

EXAMPLE 5

β-dimethylamino-β-methyl-m-trifluoromethylatroponitrile

The process of Example 1 was used with 3.3 g. of dimethylacetamide dimethyl acetal and 4.2 g. of m-trifluoromethylphenylacetonitrile to produce 4.1 g. of β-dimethylamino-β-methyl-m-trifluoromethylatroponitrile, an oily liquid.

|   | Theoretical | Found |
|---|---|---|
| C | 61.42% | 61.22% |
| H | 5.15 | 5.00 |
| N | 11.02 | 10.83 |

EXAMPLE 6

β-amino-m-trifluoromethylatroponitrile

One hundred ml. of methyl formate was cooled to 0° C., and 9.25 g. of m-trifluoromethylphenylacetonitrile and 2.7 g. of sodium methoxide were added. The mixture was allowed to warm slowly to room temperature and was stirred for 3 hours. The mixture was then evaporated to dryness, and the residue was partitioned between diethyl ether and water. The water layer was washed three times with diethyl ether, and was then acidified and finally extracted with diethyl ether. The extract was dried over sodium sulfate and was evaporated to dryness under vacuum. The residue was recrystallized from benzene-hexane to produce 7 g. of β-hydroxy-m-trifluoromethylatroponitrile, m.p. 96°–100° C.

A 6.3 g. portion of the above intermediate was dissolved in 25 ml. of methyl iodide, and 7 g. of silver oxide was added in small portions with stirring. The mixture was then stirred at reflux temperature for 1 hour and filtered. The filtrate was evaporated to dryness to give 6 g. of β-methoxy-m-trifluoromethylatroponitrile, an oily liquid.

A 2.1 g. portion of the above product was dissolved in 50 ml. of methanol, and the solution was stirred at reflux for 10 minutes while gaseous ammonia was bubbled through the mixture. The reaction mixture was then cooled and evaporated to dryness, and the residue was recrystallized from benzene-hexane to yield 1.3 g. of β-amino-m-trifluoromethylatroponitrile, m.p. 77°–79° C.

|   | Theoretical | Found |
|---|---|---|
| C | 56.61% | 56.42% |
| H | 3.33 | 3.49 |
| N | 13.20 | 13.07 |

EXAMPLE 7

β-diethylamino-m-trifluoromethylatroponitrile

The last step of the process of Example 6 was repeated, using 1.0 g. of the methoxy compound and 10 ml. of 25% aqueous diethylamine in 10 ml. of methanol to produce 0.5 g. of β-diethylamino-m-trifluoromethylatroponitrile, m.p. 59°–61° C.

|   | Theoretical | Found |
|---|---|---|
| C | 62.68% | 62.86% |
| H | 5.46 | 5.62 |
| N | 10.44 | 10.45 |

EXAMPLE 8

β-methylamino-m-trifluoromethylatroponitrile

The process of the last step of Example 6 was again used with 1 g. of the methoxy compound in 5 ml. of methanol saturated with methylamine. The product was 0.5 g. of β-methylamino-m-trifluoromethylatroponitrile, m.p. 77°–79° C.

|   | Theoretical | Found |
|---|---|---|
| C | 58.40% | 58.42% |
| H | 4.01 | 3.72 |
| N | 12.39 | 12.37 |

The compounds described above have been tested in a number of herbicidal test systems to determine the range of their herbicidal efficacy. The results produced by the compounds in the representative tests reported below are exemplary of the activity of the compounds.

Compound application rates are expressed in kilograms of the compound per hectare of land (kg./ha.) throughout this document.

Blank spaces in the tables below indicate that the compound was not tested against the named species. In the tests below, plants were rated on a 1–5 scale, on which 1 indicates normal plants and 5 indicates dead plants or no emergence. The compounds are identified by their example numbers.

Each test compound was dissolved in 1:1 acetone:ethanol at the rate of 2 g. per 100 ml. The solution also contained about 2 g. per 100 ml. of an anionic-nonionic surfactant blend. One ml. of the solution was diluted to 4 ml. with deionized water, and 1½ ml. of the resulting solution was applied to each pot, resulting in an application rate of 16.8 kg./ha. of test compound.

After the compounds were applied, the pots were moved to the greenhouse, watered as necessary, and observed and rated about 10–13 days after application of the compounds. Untreated control plants were used as standards in every test. The table below reports results of testing typical compounds of the invention.

Table

| Compound of Example No. | Preemergence | | | Postemergence | | |
|---|---|---|---|---|---|---|
| | Tomato | Large Crabgrass | Pigweed | Tomato | Large Crabgrass | Pigweed |
| 1 | 4 | 4 | 3 | 4 | 3 | 3 |
| 2 | 4 | 4 | 4 | 4 | 4 | 4 |
| 3 | 4 | 4 | 4 | 4 | 4 | 3 |
| 4 | 4 | 4 | 4 | 3 | 4 | 4 |
| 5 | 5 | 5 | 5 | 3 | 4 | 3 |
| 6 | 2 | 2 | 2 | | 3 | 3 |
| 8 | 4 | 4 | 3 | 4 | 4 | 4 |

Test 1

Broad spectrum greenhouse test

Square plastic pots were filled with a sandy sterilized greenhouse soil and were planted to seeds of tomato, large crabgrass and pigweed. Each pot was individually fertilized.

Test compounds were applied postemergence to some pots and preemergence to others. Postemergence applications of the compounds were sprayed over the emerged plants about 12 days after the seeds were planted. Preemergence applications were sprayed on the soil the day after the seeds were planted.

TEST 2

Multi-species greenhouse test

The test was conducted in general like the test above. The seeds were planted in flat metal trays, rather than in pots. The compounds were formulated according to the procedure above, except that about 6 g./100 ml. of the compound was dissolved in the surfactant-containing solvent, and the organic solution was diluted with appropriate amounts of water before application to the trays. The compounds were applied at various rates which are indicated in the table below and the results of testing against the species named below are as follows.

| Compound of Example No. | Rate of Appln. kg./ha. | Preemergence | | | | | | | | | | |
|---|---|---|---|---|---|---|---|---|---|---|---|---|
| | | Corn | Cotton | Soybean | Wheat | Alfalfa | Sugar beet | Rice | Cucumber | Tomato | Barnyard Grass | Lambsquarter |
| 1 | 9.0 | 1 | | | | | | | | | | |
| 2 | 2.2 | 1 | 1 | 1 | 3 | 2 | 1 | 1 | 2 | 3 | 5 | 2 |
|   | 4.5 | 2 | 1 | 1 | 3 | 2 | 3 | 2 | 4 | 4 | 5 | 4 |
|   | 9.0 | 1 | | | | | | | | | | |
| 3 | 4.5 | 1 | 2 | 2 | 1 | 1 | 2 | 1 | 1 | 1 | 2 | 4 |
|   | 9.0 | 2 | | | | | | | | | | |
| 4 | 9.0 | 1 | | | | | | | | | | |
| 5 | 2.2 | 1 | 1 | 1 | 2 | 1 | 2 | 1 | 2 | 4 | 2 | 4 |
|   | 9.0 | 2 | | | | | | | | | | |
| 6 | 9.0 | 1 | | | | | | | | | | |
| 7 | 2.2 | 1 | 1 | 1 | 1 | 1 | 2 | 1 | 2 | 1 | 2 | 3 |
|   | 4.5 | 1 | 1 | 1 | 1 | 2 | 3 | 1 | 3 | 2 | 2 | 4 |
|   | 9.0 | 1 | | | | | | | | | | |
| 8 | 9.0 | 1 | | | | | | | | | | |

| Compound of Example No. | Rate of Appln. kg./ha. | Preemergence | | | | | | | | |
|---|---|---|---|---|---|---|---|---|---|---|
| | | Large Crabgrass | Mustard | Pigweed | Foxtail | Wild Oat | Velvetleaf | Jimsonweed | Morning-glory | Zinnia |
| 1 | 9.0 | 3 | | 3 | 2 | | 1 | | 1 | 1 |
| 2 | 2.2 | 3 | 1 | 3 | 3 | 2 | 2 | 2 | 1 | 2 |
|   | 4.5 | 5 | 2 | 4 | 4 | 2 | 4 | 2 | 1 | 2 |
|   | 9.0 | 5 | | 4 | 3 | | 3 | | 1 | 1 |
| 3 | 4.5 | 5 | 3 | 4 | 2 | 1 | 1 | 1 | 1 | 1 |
|   | 9.0 | 4 | | 3 | 3 | | 2 | | 3 | 5 |
| 4 | 9.0 | 4 | | 2 | 3 | | 1 | | 1 | 1 |
| 5 | 2.2 | 5 | 3 | 3 | 2 | 3 | 2 | 2 | 1 | 2 |
|   | 9.0 | 4 | | 5 | 3 | | 3 | | 2 | 2 |
| 6 | 9.0 | 1 | | 2 | 1 | | 1 | | 1 | 1 |

-continued

| 7 | 2.2 | 4 | 2 | 4 | 2 | 2 | 1 | 1 | 1 | 1 |
|---|-----|---|---|---|---|---|---|---|---|---|
|   | 4.5 | 5 | 2 | 5 | 3 | 2 | 1 | 2 | 1 | 1 |
|   | 9.0 | 5 |   | 5 | 3 |   | 2 |   | 2 | 1 |
| 8 | 9.0 | 3 |   | 3 | 2 |   | 2 |   | 1 | 1 |

|  |  | Postemergence | | | | | |
|---|---|---|---|---|---|---|---|
| Compound of Ex. No. | Rate of Appln. kg./ha. | Corn | Large Crabgrass | Pigweed | Foxtail | Velvet- Leaf | Morning glory | Zinnia |
| 1 | 9.0 | 1 | 2 | 3 | 2 | 2 | 2 | 2 |
| 2 | 9.0 | 2 | 3 | 2 | 3 | 3 | 3 | 3 |
| 3 | 9.0 | 2 | 2 | 2 | 2 | 2 | 2 | 2 |
| 4 | 9.0 | 2 | 3 | 2 | 2 | 2 | 2 | 2 |
| 5 | 9.0 | 2 | 4 | 3 | 2 | 3 | 2 | 2 |
| 6 | 9.0 | 2 | 2 | 3 | 2 | 3 | 2 | 3 |
| 7 | 9.0 | 2 | 2 | 2 | 2 | 2 | 2 | 2 |
| 8 | 9.0 | 2 | 2 | 3 | 2 | 2 | 2 | 2 |

The broad spectrum activity of the compounds of this invention is illustrated by the above examples. The test results point up the efficacy of the compounds against both grasses and broadleafed plants. Plant scientists will recognize that the exemplified activity of the compounds shows that they are broadly effective against unwanted herbaceous plants, which will be referred to as weeds, for the sake of brevity.

As the above test results demonstrate, the compounds are used to reduce the vigor of weeds by contacting them with an herbicidally-effective amount of one of the compounds. The term "reduce the vigor of" is used to refer to both killing and injuring the weed which is contacted with a compound. In some instances, as is clear from the test results, the whole population of the contacted weed is killed. In other instances, part of the weeds are killed and part of them are injured, and in still other instances, none of the weeds are killed but are merely injured by application of the compound. It will be understood that reducing the vigor of the weed population by injuring part of them is beneficial, even though part of the population survives application of the compound. The weeds, the vigor of which has been reduced, are unusually susceptible to the stresses which normally afflict plants, such as disease, drought, lack of nutrients and so forth.

Thus, the treated weeds are likely to expire due to stress of the environment, even though they survive application of the compound. Further, if the treated weeds are growing in cropland, the crop, as it grows normally, tends to shade out the treated weeds of reduced vigor. Therefore, the crop has a great advantage over the treated weeds in the competition for nutrients and sunlight. Still further, when the treated weeds are growing in fallow land, or industrial property which is desired to be bare, the reduction in their vigor necessarily tends to minimize the treated weeds' consumption of water and nutrients, and also minimizes the fire hazard and nuisance which the weeds present.

The compounds are herbicidally effective when applied both preemergence and postemergence. Thus, they can be used both by direct contact of the compounds with emerged weeds, and by applying the compounds to the soil, where they come into contact with germinating and emerging weeds. Preemergence application of the compounds, wherein the germinating and emerging weeds are contacted with the compound through soil application, is preferred.

Accordingly, this invention is a method of reducing the vigor of weeds which comprises contacting the weeds with an herbicidally-effective amount of a compound described above. The term herbicidally-effective amount refers to an amount which will reduce the vigor of the treated weed. In the context of this invention, weed seeds, which are contacted with the compounds by application of the compounds to the soil, are regarded as weeds.

Amounts of herbicides are measured in terms of the weight of herbicide applied per unit area, usually called the application rate. The best application rate of a given compound of the invention for the control of a given weed varies, of course, depending upon the climate, soil texture, water and organic matter contents of the soil and other factors known to those skilled in plant science. It will be found, however, that the optimum application rate is usually in the range from about 1.0 to about 20 kg./ha.

It is not implied, of course, that all compounds of this invention are effective against all weeds at all rates. Some compounds are more effective against some types of weeds, other compounds are more effective against other types. All of the compounds, however, are effective against at least some weeds. It is within the ordinary skill of a plant scientist to ascertain the weeds which are most advantageously controlled with the various compounds, and the best application rate for the particular use.

The compounds are applied to the soil or to emerged weeds in the manners usual in agriculture. It is best to apply the compounds in the form of the herbicidal compositions which are important embodiments of the present invention. They may be applied to the soil in the form of either water-dispersed or granular compositions, the preparation of which will be discussed below. Usually, water-dispersed compositions will be used for the application of the compounds to emerged weeds. The compositions are applied with any of the many types of sprayers and granular applicators which are in wide use for the distribution of agricultural chemicals over soil or standing vegetation. In general, the compositions are formulated in the manners usual in agricultural chemistry.

Very often, the compounds are formulated as concentrated compositions which are applied either to the soil or the foliage in the form of water dispersions or emulsions containing in the range of from about 0.1 percent to about 5 percent of the compound. Water-dispersible or emulsifiable compositions are either solids usually known as wettable powders, or liquids usually known as emulsifiable concentrates. Wettable powders comprise an intimate, finely-divided mixture of the compound, an inert carrier, and surfactants. The concentration of the compound is usually from about 10 percent to about 90 percent. The inert carrier is usually chosen from among the attapulgite clays, the montmorillonite clays, the kaolin clays, the diatomaceous earths and the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates and nonionic surfactants such as ethylene oxide adducts of phenol.

Typical emulsifiable concentrates of the new compounds comprise a convenient concentration of the compound, such as from about 100 to about 500 g. per liter of liquid, dissolved in an inert carrier which is a mixture of water-immiscible solvent and emulsifiers. Useful organic solvents include the aromatics, especially the xylenes, and the petroleum fractions, especially the high-boiling naphthalenic and olefinic portions of petroleum. Many other organic solvents may also be used such as the terpenic solvents, and the complex alcohols such as 2-ethoxyethanol. Suitable emulsifiers for emulsifiable concentrates are chosen from the same types of surfactants used for wettable powders.

When a compound is to be applied to the soil, as for a preemergence application of the compound, it is convenient to use a granular formulation. Such a formulation typically comprises the compound dispersed on a granular inert carrier such as coarsely ground clay. The particle size of granules usually ranges from about 0.1 to about 3 mm. The usual formulation process for granules comprises dissolving the compound in an inexpensive solvent and applying the solution to the carrier in an appropriate solids mixer. Somewhat less economically, the compound may be dispersed in a dough composed of damp clay or other inert carrier, which is then dried and coarsely ground to produce the desired granular product.

It has become customary in agricultural chemistry to apply two or even more agricultural chemicals simultaneously in order to control weeds of many different types, or weeds and other pests, with a single application of chemicals. The compounds of this invention lend themselves well to combination with other agricultural chemicals and may usefully be combined with insecticides, fungicides, nematicides and other herbicides as may be desirable.

I claim:
1. A method of reducing the vigor of weeds which comprises contacting the weeds with an herbicidally-effective amount of a compound of the formula

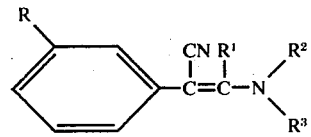

wherein R represents
hydrogen,
chloro,
fluoro,
bromo or
trifluoromethyl;
$R^1$, $R^2$ and $R^3$ independently represent hydrogen, methyl or ethyl.

2. A method of claim 1 wherein the amount of the compound is from about 1.0 to about 20 kg./ha.

3. The method of claim 2 wherein the compound is β-dimethylamino-m-trifluoromethylatroponitrile.

4. The method of claim 2 wherein the compound is β-dimethylamino-m-fluoroatroponitrile.

5. The method of claim 2 wherein the compound is m-chloro-β-dimethylaminoatroponitrile.

6. The method of claim 2 wherein the compound is β-dimethylamino-β-methyl-m-trifluoromethylatroponitrile.

7. The method of claim 2 wherein the compound is β-diethylamino-m-trifluoromethylatroponitrile.

* * * * *